United States Patent
Hibbard

(10) Patent No.: US 11,517,768 B2
(45) Date of Patent: Dec. 6, 2022

(54) SYSTEMS AND METHODS FOR DETERMINING RADIATION THERAPY MACHINE PARAMETER SETTINGS

(71) Applicant: Elekta, Inc., St. Charles, MO (US)

(72) Inventor: Lyndon S. Hibbard, Atlanta, GA (US)

(73) Assignee: Elekta, Inc., Atlanta, GA (US)

( * ) Notice: Subject to any disclaimer, the term of this patent is extended or adjusted under 35 U.S.C. 154(b) by 1050 days.

(21) Appl. No.: 15/658,484

(22) Filed: Jul. 25, 2017

(65) Prior Publication Data

US 2019/0030370 A1    Jan. 31, 2019

(51) Int. Cl.
*A61N 5/10* (2006.01)
*G16H 30/40* (2018.01)
(Continued)

(52) U.S. Cl.
CPC ......... *A61N 5/1038* (2013.01); *A61N 5/1031* (2013.01); *A61N 5/1039* (2013.01);
(Continued)

(58) Field of Classification Search
CPC .. A61N 5/1038; A61N 5/1031; A61N 5/1039; A61N 5/1045; A61N 5/1067;
(Continued)

(56) References Cited

U.S. PATENT DOCUMENTS

| | | | | |
|---|---|---|---|---|
| 9,042,620 | B2 * | 5/2015 | Kohlberger | ........ G06K 9/6209 382/131 |
| 11,077,320 | B1 | 8/2021 | Hibbard | |

(Continued)

FOREIGN PATENT DOCUMENTS

| | | |
|---|---|---|
| CN | 102316930 A | 1/2012 |
| CN | 103961182 A | 8/2014 |

(Continued)

OTHER PUBLICATIONS

S. Miao, Z. J. Wang, Y. Zheng and R. Liao, "Real-time 2D/3D registration via CNN regression," 2016 IEEE 13th International Symposium on Biomedical Imaging (ISBI), Prague, 2016, pp. 1430-1434. (Year: 2016).*

(Continued)

*Primary Examiner* — Brent Johnston Hoover
(74) *Attorney, Agent, or Firm* — Schwegman Lundberg & Woessner, P.A.

(57) ABSTRACT

Systems and methods can include a method for training a deep convolutional neural network to provide a patient radiation treatment plan, the method comprising collecting patient data from a group of patients, the patient data including at least one image of patient anatomy and a prior treatment plan, wherein the treatment plan includes predetermined machine parameters, and training a deep convolution neural network for regression by using the prior treatment plans and the corresponding collected patient data to determine a new treatment plan. Systems and methods can also include a method of using a deep convolutional neural network to provide a radiation treatment plan, the method comprising retrieving a trained deep convolution neural network previously trained on patient data from a group of patients, collecting new patient data, wherein the new patient data includes at least one image of patient anatomy, and determining a new treatment plan for the new patient using the trained deep convolutional neural network for regression, wherein the new treatment plan has a new set of machine parameters.

24 Claims, 11 Drawing Sheets

(51) Int. Cl.
  *G16H 20/40* (2018.01)
  *G16H 10/60* (2018.01)
  *G06N 3/04* (2006.01)
  *G06N 3/08* (2006.01)

(52) U.S. Cl.
  CPC ......... *A61N 5/1045* (2013.01); *A61N 5/1067* (2013.01); *G06N 3/04* (2013.01); *G06N 3/08* (2013.01); *G16H 10/60* (2018.01); *G16H 20/40* (2018.01); *G16H 30/40* (2018.01); *A61N 2005/1041* (2013.01)

(58) Field of Classification Search
  CPC ........... A61N 2005/1041; G16H 20/40; G16H 10/60; G16H 30/40; G06N 3/04; G06N 3/08
  See application file for complete search history.

(56) References Cited

U.S. PATENT DOCUMENTS

| | | |
|---|---|---|
| 2008/0298550 A1 | 12/2008 | Otto |
| 2012/0136194 A1 | 5/2012 | Zhang et al. |
| 2012/0230572 A1 | 9/2012 | Kohlberger et al. |
| 2013/0014231 A1 | 6/2013 | Fahimian et al. |
| 2014/0031603 A1 | 1/2014 | Robar et al. |
| 2016/0213948 A1* | 7/2016 | Renne ................. A61N 5/1039 |
| 2016/0217595 A1* | 7/2016 | Han ..................... G06T 7/0012 |
| 2017/0177812 A1 | 6/2017 | Sjolund |
| 2018/0078784 A1* | 3/2018 | Schnarr ............... A61N 5/1031 |
| 2018/0154179 A1 | 6/2018 | Ollila et al. |
| 2018/0185672 A1 | 7/2018 | Ramezanzadeh Moghadam |
| 2018/0315188 A1* | 11/2018 | Tegzes ................ G06K 9/2054 |
| 2019/0318474 A1 | 10/2019 | Han |
| 2019/0333623 A1 | 10/2019 | Hibbard |
| 2021/0244971 A1 | 8/2021 | Hibbard |
| 2021/0308487 A1 | 10/2021 | Hibbard |

FOREIGN PATENT DOCUMENTS

| | | | |
|---|---|---|---|
| CN | 105120955 A | 12/2015 | |
| CN | 105358217 A | 2/2016 | |
| CN | 110944717 A | 3/2020 | |
| CN | 111494810 B | 10/2021 | |
| CN | 114206438 A | 3/2022 | |
| EP | 2605828 A2 * | 6/2013 | ............. A61N 5/103 |
| EP | 3010585 A1 * | 4/2016 | ............. A61N 5/103 |
| EP | 3658231 B1 | 4/2022 | |
| JP | 201150201 A | 1/2011 | |
| WO | 2014205128 | 12/2014 | |
| WO | 2016081916 | 5/2016 | |
| WO | WO-2018048507 A1 * | 3/2018 | ........... A61B 5/0035 |
| WO | 2019023142 | 1/2019 | |
| WO | WO-2019212804 A1 | 11/2019 | |
| WO | WO-2020256750 A1 | 12/2020 | |
| WO | WO-2021159143 A1 | 8/2021 | |

OTHER PUBLICATIONS

U.S. Appl. No. 62/488,442, filed Apr. 2017, Tegzes.*
Nie et al., "Estimating CT Image from MRI Data Using 3D Fully Convolutional Networks", 2016, Deep Learn Data Label Med Appl (2016), pp. 1-12. (Year: 2016).*
"Imagenet", Stanford University Vision Lab, Accessed from Internet on Nov. 9, 2018 http://www.image-net.org/, (2016), 1 pg.
"VRad Deep Learning Algorithm Successfully Identifies Potential Intracranial Hemorrhaging (product announcement", https://www.vrad.com, Retrieved from internet: https://www.itnonline.com/content/vrad-deep-learning-algorithm-successfully-identifies-potential-intracranial-hemorrhaging, (Dec. 14, 2015), 2 pgs.
Bishop, Christopher M., "Pattern Recognition and Machine Learning", Springer-Verlag New York, (2006), 758 pgs.
Goodfellow, Ian, et al., "Deep learning", vol. 1. Cambridge: MIT press, (2016), 802 pgs.
Appenzoller, Lindsey M., et al., "Predicting dose-volume histograms for organs-at-risk in IMRT planning", Med. Phys. 39 (12), (Dec. 2012), pp. 7446-7461.
Breedveld,, Sebastiaan, et al., "The equivalence of multi-criteria methods for radiotherapy plan optimization", Phys. Med. Biol. 54 (2009), (Nov. 17, 2009), pp. 7199-7209.
Bukovsky, Ivo, et al., "A Fast Neural Network Approach to Predict Lung Tumor Motion during Respiration for Radiation Therapy Applications", BioMed Research International vol. 2015, Article ID 489679, (2015), 3 pgs.
Dobler, Barbara, et al., "Direct machine parameter optimization for intensity modulated radiation therapy (IMRT) of oropharyngeal cancer—a planning study", Journal of Applied Clinical Medical Physics, vol. 10, No. 4,, (Fall 2009), pp. 4-15.
Hardemark, Bjorn, et al., "Direct machine parameter optimization", Philips Medical Systems part Royal Philips Electronics whitepaper, (2004), 8 pgs.
Ibragimov, B., et al., "Development of a Novel Deep Learning Algorithm for Autosegmentation of Clinical Tumor Volume and Organs at Risk in Head and Neck Radiation Therapy Planning", S226 International Journal of Radiation Oncology Biology Physics, (Oct. 1, 2016), p. 1147.
Ibragimov, B., et al., "Machine-Learning Based Segmentation of Organs at Risks for Head and Neck Radiotherapy Planning", [Online]. Retrieved from the Internet:<URL: http://onlinelibrary.wiley.com/doi/10.1118/1.4958186/full>, (Jun. 2016).
Kang, John, et al., "Machine Learning Approaches for Predicting Radiation Therapy Outcomes: A Clinician's Perspective", International Journal of Radiation Oncology Biology Physics, (Jul. 27, 2015), pp. 1127-1135.
Krizhevsky, Alex, et al., "Imagenet classification with deep convolutional neural networks", Advances in neural information processings systems, (2012), 1-9.
Kunze-Busch, M., et al., "Efficient SIB-IMRT planning of head and neck patients with Pinnacle—DMPO", MEDICAMUNDI 51/2+3 Nov. 2007, (Nov. 2007), pp. 95-99.
Lecun, Yann, et al., "Deep Learning", Nature vol. 521, (May 28, 2015), pp. 436-444.
Park, Seonyeong, et al., "Intra and Inter Fractional Variation Prediction of Lung Tumors Using Fuzzy Deep Learning", IEEE journal of Transitional Engineering in Health and Medicine, (Jan. 8, 2016), 12 pgs.
Romeijn, Edwin H, et al., "A unifying framework for multi-criteria fluence map optimization models", Phys. Med. Biol. 49 (2004), (May 4, 2004), pp. 1991-2013.
Ronneberger, Olaf, et al., "U-Net Convolutional Networks for Biomedical Image Segmentation", Computer Science Department and BIOSS Centre for Biological Signalling Studies, University of Freiburg, Germany, (May 18, 2015), 8 pgs.
Shin, Hoo-Chang, et al., "Learning to Read Chest X-Rays: Recurrent Neural Cascade Model for Automated Image Annotation", National Institutes of Health, Bethesda, 20892-1182, (Mar. 28, 2016), 14 pgs.
Unkelbach, Jan, et al., "Optimization approaches to volumetric modulated arc therapy planning", Am. Assoc. Phys. Med. 42 (3), (Mar. 2015), 12 pgs.
Wu, Binbin, et al., "Patient geometry-driven information retrieval for IMRT treatment plan quality control", Am Assoc Phys Med 36 12, (Nov. 6, 2009).
Zarepisheh, Masoud, et al., "A multicriteria framework with voxel dependent parameters for radiotherapy treatment plan optimization", Am. Assoc. Phys. Med.41 (4), (Apr. 2014), 11 pgs.
Zhu, N, et al., "Deep Convolutional Neural Network Image Matching for Ultrasound Guidance in Radiotherapy", [Online], Retrieved from the Internet: <URL: http://onlinelibrary.wiley.com/doi/10.1118/1.4955603/abstract>, (Jun. 2016).
Zhu, Xiaofeng, et al., "A planning quality evaluation tool for prostate adaptive IMRT based on machine learning", Am. Assoc. Phys. Med. 38 2, (Feb. 2011), pp. 719-726.
Zuley, M L, et al., "Applying machine learning to radiotherapy planning for head & neck cancer", [Online] Retrieved from the

(56) References Cited

OTHER PUBLICATIONS

Internet <URL:https://deepmind.com/blog/applying-machine-learning-radiotherapy-planning-head-neck-cancer/>, (Aug. 30, 2016), 3 pgs.
"International Application Serial No. PCT US2018 043320, Written Opinion dated Oct. 29, 2018", 7 pgs.
"International Application Serial No. PCT US2018 043320, International Search Report dated Oct. 29, 2018", 6 pgs.
Nie, Dong, "Estimating CT Image from MRI Data Using 3D Fully Convolutional Networks", (Sep. 27, 2016), 9 pgs.
"Conditional Generative Adversarial Nets in TensorFlow", Agustinus Kristiadi's Blog, [Online]. Retrieved from the Internet: <URL: https://wiseodd.github.io/techblog/2016/12/24/conditional-gan-tensorflow/ >, 6 pgs.
"International Application Serial No. PCT/US2018/043320, International Preliminary Report on Patentability dated Feb. 6, 2020", 9 pgs.
"International Application Serial No. PCT/US2019/028720, International Search Report dated Oct. 16, 2019", 4 pgs.
"International Application Serial No. PCT/US2019/028720, Written Opinion dated Oct. 16, 2019", 8 pgs.
"Ray Tracing (graphics)", Wikipedia https://en.wikipedia.org/wiki/Ray_tracing_(graphics), (2019), 15 pgs.
Abadi, Martin, et al., "Tensorflow: Large-scale machine learning on heterogeneous distributed systems", arXiv preprint arXiv:1603.04467, (2016), 19 pgs.
Appenzoller, Lindsey M., et al., "Predicting dose-volume histograms for organs-at-risk in IMRT planning", Medical physics 39.12, (2012), 7446-7461.
Babier, A, et al., "Knowledge-based automated planning with three-dimensional generative adversarial networks", Medical Physics, (Dec. 21, 2018), 15 pgs.
Breedveld, Sebastiaan, et al., "The equivalence of multi-criteria methods for radiotherapy plan optimization", Physics in Medicine & Biology 54.23, (2009), 7199-7209.
Chris, McIntosh, et al., "Fully automated treatment planning for head and neck radiotherapy using a voxel-based dose prediction and dose mimicking method", Physics in Medicine & Biology, vol. 62, No. 15, XP055416743, (Sep. 2, 2016), 5926-5944.
Creswell, Antonia, et al., "Generative Adversarial Networks: An Overview", IEEE Signal Processing Magazine 35.1, (2018), 53-65.
Glassner, A S, "An Introduction to Ray Tracing", Morgan-Kauffman Part 1 out of 2, (1989), 177 pgs.
Glassner, A S, "An Introduction to Ray Tracing", Morgan-Kauffman Part 2 out of 2, (1989), 176 pgs.
Goodfellow, Ian, et al., "Generative Adversarial Nets", Advances in Neural Information Processing Systems 27, Curran Associates, Inc., (Jun. 10, 2014), 9 pgs.
Goodfellow, Ian, "NIPS 2016 tutorial: Generative adversarial networks", arXiv preprint arXiv:1701.00160, (2016), 57 pgs.
Hastie, Trevor, et al., "The elements of statistical learning: data mining, inference, and prediction", Springer series in statistics, (2001), 764 pgs.
He, Kaiming, et al., "Identity mappings in deep residual networks", European Conference on Computer Vision. Springer, Cham, (2016), 15 pgs.
Hesse, Christopher, "Image-to-Image Translation in Tensorflow Make discriminators do your work for you", [Online]. Retrieved from the Internet: <URL: https://affinelayer.com/pix2pix/>, (Jan. 25, 2017), 12 pgs.
Isola, Phillip, et al., "Image-to-Image Translation with Conditional Adversarial Networks", arXiv:1611.07004 [cs.CV], (Nov. 22, 2017), 17 pgs.
Johnson, Hans J, et al., "The ITK Software Guide", (Jul. 25, 2019), 997 pgs.
Kak, A C, et al., "Principles of Computerized Tomographic Imaining Chapter 1", SIAM Philadelphia, (2001), 4 pgs.
Kak, A C, et al., "Principles of Computerized Tomographic Imaining Chapter 2", SIAM Philadelphia, (2001), 43 pgs.
Kak, A C, et al., "Principles of Computerized Tomographic Imaining Chapter 3", SIAM Philadephia, (2001), 64 pgs.
Kak, A C, et al., "Principles of Computerized Tomographic Imaining Chapter 4", SIAM Philadelphia, (2001), 63 pgs.
Kak, A C, et al., "Principles of Computerized Tomographic Imaining Chapter 5", SIAM Philadelphia, (2001), 25 pgs.
Kak, A C, et al., "Principles of Computerized Tomographic Imaining Chapter 6", SIAM Philadelphia, (2001), 71 pgs.
Kak, A C, et al., "Principles of Computerized Tomographic Imaining Chapter 7", SIAM Philadelphia, (2001), 22 pgs.
Kak, A C, et al., "Principles of Computerized Tomographic Imaining Chapter 8", SIAM Philapelphia, (2001), 26 pgs.
Kak, A C, et al., "Principles of Computerized Tomographic Imaining Index", SIAM Philadelphia, (2001), 6 pgs.
Kak, A C, et al., "Principles of Computerized Tomographic Imaining Introduction", Siam Philadelphia, (2001), 9 pgs.
Krizhevsky, Alex, et al., "Imagenet classification with deep convolutional neural networks", Advances in neural information processing systems, (2012), 9 pgs.
Lecun, Yann, et al., "Deep learning", Nature, vol. 521. 7553, (2015), 436-444.
McIntosh, C, et al., "Contextual Atlas Regression Forests: Multiple-Atlas-Based Automated Dose Prediction in Radiation Therapy", IEEE Transactions on Medical Imaging, 15 pgs.
Mirza, Mehdi, et al., "Conditional generative adversarial nets", arXiv preprint arXiv:1411.1784, (2014), 7 pgs.
Murphy, Kevin P, "Machine Learning A Probabilistic Perspective", MIT Press, Cambridge, MA, USA Part 2 out of 2, (2012), 549 pgs.
Nguyen, D, et al., "A feasibility study for predicting optimal radiation therapy dose distributions of prostate cancer patients from patient anatomy using deep learning", Scientific Reports www.nature.com/scientificreports, (Jan. 31, 2019), 10 pgs.
Nguyen, Dan, et al., "Dose Prediction with U-net: A Feasibility Study for Predicting Dose Distributions from Contours using Deep Learning on Prostate IMRT Patients", arXiv preprint arXiv:1709.09233, (2017), 17 pgs.
Rafid, Mahmood, et al., "Automated Treatment Planning in Radiation Therapy using Generative Adversarial Networks", Arxiv.Org, Cornell University Library, 201 Olin Library Cornell University Ithaca, NY 14853, XP081113459, (Jul. 17, 2018), 15 pgs.
Rit, S, et al., "The Reconstruction Toolkit (RTK), an open-source cone-beam CT reconstruction toolkit based o", 5 pgs.
Ronneberger, Olaf, et al., "U-net: Convolutional networks for biomedical image segmentation", International Conference on Medical image computing and computer-assisted intervention. Springer, Cham, (2015), 1-8.
Shirashi, S, et al., "Knowledge-based prediction of three-dimensional dose distributions for external beam radiotherapy", Medical Physics, 43(1), (2015), 378-287.
Shirley, P, et al., "Fundamentals of Computer Graphics", Chapter 10 Ray Tracing AK Peters, (2005), 785 pgs.
Tseng, Huan-Hsin, et al., "Deep reinforcement learning for automated radiation adaptation in lung cancer", Medical physics 44.12, (2017), 6690-6705.
Wachowicz, K, et al., "On the direct acquisition of beam's-eye-view mages in MRI for integration with external beam radiotherapy", Physics in Medicine, 11 pgs.
Wu, Binbin, et al., "Patient geometry-driven information retrieval for IMRT treatment plan quality control", Medical physics 36.12, (2009), 5497-5505.
Zarepisheh, Masoud, et al., "A DVH-guided IMRT optimization algorithm for automatic treatment planning and adaptive radiotherapy replanning", Medical physics 41,6Part1, (2014), 061711-1-061711-14.
Zhu, Jun-Yan, et al., "Unpaired Image-to-Image Translation using Cycle-Consistent Adversarial Networks", IEEE International Conference on Computer Vision, (2017), 10 pgs.
Zhu, Xiaofeng, et al., "A planning quality evaluation tool for prostate adaptive IMRT based on machine learning", Medical physics 38.2, (2011), 719-726.
"Beam's Eye View", Wikipedia https: en.wikipedia.org wiki Beam% 27s_eye_view, (Accessed on Mar. 13, 2020), 1 pg.
"International Application Serial No. PCT US2019 039830, International Search Report dated Mar. 13, 2020", 4 pgs.

(56) References Cited

OTHER PUBLICATIONS

"International Application Serial No. PCT US2019 039830, Written Opinion dated Mar. 13, 2020", 5 pgs.
"Australian Application Serial No. 2018307739, First Examination Report dated Oct. 14, 2020", 5 pgs.
"Australian Application Serial No. 2018307739, Response filed Jan. 20, 2021 First Examination Report dated Oct. 14, 2020", 29 pgs.
"European Application Serial No. 18752372.5 Response to Communication pursuant to Rules 161(1) and 162 EPC filed Sep. 16, 2020", 16 pgs.
"U.S. Appl. No. 16/784,919, Corrected Notice of Allowability dated May 19, 2021", 4 pgs.
"U.S. Appl. No. 16/784,919, Notice of Allowance dated Apr. 15, 2021", 10 pgs.
"Chinese Application Serial No. 201880049758.0, Office Action dated Mar. 3, 2021", w/ English translation, 22 pgs.
"European Application Serial No. 18752372.5, Communication Pursuant to Article 94(3) EPC dated Mar. 2, 2021", 3 pgs.
"European Application Serial No. 18752372.5, Response filed Mar. 25, 2021 to Communication Pursuant to Article 94(3) EPC dated Mar. 2, 2021", 18 pgs.
"Japanese Application Serial No. 2020-503934, Notification of Reasons for Refusal dated Mar. 2, 2021", w/ English translation, 10 pgs.
"U.S. Appl. No. 16/784,919, Corrected Notice of Allowability dated Jun. 30, 2021", 4 pgs.
"Chinese Application Serial No. 201880049758.0, Response filed Jun. 30, 2021 to Office Action dated Mar. 3, 2021", With English claims, 19 pages.
"International Application Serial No. PCT/US2021/070119, International Search Report dated May 19, 2021", 5 pgs.
"International Application Serial No. PCT/US2021/070119, Written Opinion dated May 19, 2021", 6 pgs.
"Japanese Application Serial No. 2020-503934, Response filed Jun. 25, 2021 to Notification of Reasons for Refusal dated Mar. 2, 2021", With English claims, 12 pages.
Hibbard, Lyndon, et al., "Adversarial Prediction of Radiotherapy Treatment Machine Parameters", Advances in Intelligent Data Analysis XIX; [Lecture Notes in Computer Science; Lect.Notes Computer], Springer International Publishing, Cham,, (Oct. 1, 2020), 85-94.
"Chinese Application Serial No. 201880049758.0, Office Action dated Sep. 15, 2021", With English translation, 22 pages.
"Chinese Application Serial No. 201880049758.0, Office Action dated Feb. 9, 2022", w/ English translation, 10 pgs.
"Chinese Application Serial No. 201880049758.0, Office Action dated Apr. 20, 2022", W/English Translation, 22 pgs.
"Chinese Application Serial No. 201880049758.0, Response filed Mar. 16, 2022 to Office Action dated Feb. 9, 2022", w/ English Claims, 20 pgs.
"Chinese Application Serial No. 201880049758.0, Response filed Nov. 28, 2021 to Office Action dated Sep. 15, 2021", w English Claims, 21 pgs.
"International Application Serial No. PCT US2019 039830, International Preliminary Report on Patentability dated Dec. 30, 2021", 7 pgs.
U.S. Appl. No. 17/596,263, filed Dec. 6, 2021, Predicting Radiotherapy Control Points Using Projection Images.
U.S. Appl. No. 16/784,919 U.S. Pat. No. 11,077,320, filed Feb. 7, 2020, Adversarial Prediction of Radiotherapy Treatment Plans.
U.S. Appl. No. 17/304,500, filed Jun. 22, 2021, Adversarial Prediction of Radiotherapy Treatment Plans.
"European Application Serial No. 19740293.6, Response to Communication pursuant to Rules 161 and 162 filed Jun. 13, 2022", 14 pgs.
"Chinese Application Serial No. 201880049758.0, Response filed Jun. 16, 2022 to Decision of Rejection dated Apr. 20, 2022", with English machine translation, Claims not amended in response filed, 15 pgs.

* cited by examiner

SYSTEMS AND METHODS FOR DETERMINING RADIATION THERAPY MACHINE PARAMETER SETTINGS

TECHNICAL FIELD

Embodiments of the present invention pertain generally to determining machine parameters in a radiation therapy treatment system. In particular, the present invention pertains to using deep learning technologies to determine machine parameters for a treatment plan in a radiation therapy system.

BACKGROUND

Radiation therapy or "radiotherapy" can be used to treat cancers or other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator). The intensity and shape of the radiation beam can be adjusted by collimation avoid damaging healthy tissue (e.g., organs at risk) adjacent to the targeted tissue by conforming the projected beam to a profile of the targeted tissue.

The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays. Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor(s). The health care provider can delineate the target tumor that is to receive a prescribed radiation dose using a manual technique, and the health care provider can similarly delineate nearby tissue, such as organs, at risk of damage from the radiation treatment. Alternatively or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs).

The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare. The treatment plan can then be later executed by positioning the patient in the treatment machine and delivering the prescribed radiation therapy. The radiation therapy treatment plan can include dose "fractioning," whereby a sequence of radiation therapy deliveries are provided over a predetermined period of time (e.g., 45 fractions), with each therapy delivery including a specified fraction of a total prescribed dose. However, during treatment the position of the patient and the position of the target tumor in relation to the treatment machine (e.g., linear accelerator—"linac") is very important in order to ensure the target tumor and not healthy tissue is irradiated.

OVERVIEW

Intensity modulated radiotherapy (IMRT) and volumetric modulated arc therapy (VMAT) have become the standards of care in modern cancer radiation therapy. Determining individual patient IMRT or VMAT treatment plans can include a trial-and-error process, and can include weighing target dose versus organ at risk (OAR) sparing tradeoffs, and adjusting program constraints where effects of the program constraints on the plan quality metrics and the dose distribution can be very difficult to predict. The order in which the planning constraints can be adjusted can introduce dose differences. Treatment plan quality can depend on subjective judgements by the dosimetrist that can depend on an experience or skill level of the dosimetrist. Even the most skilled dosimetrists still have no assurances that their plans are close to optimal, or whether a little or a lot of effort will result in a better plan. In certain approaches, a computationally intensive algorithm can be used to determine a treatment plan, however such approaches can require hours to compute a treatment plan. Computational approaches can include comparing one-dimensional target-organ overlap measures in a new patient (DVHs, OVHs) with overlap measures associated with high-quality plans from previous patients to find plans similar to that of the new patient, and exploring plan quality space to determine optimal, or even Pareto-optimal, families of plans that the dosimetrist may then select for use in a radiation therapy treatment. The present inventors have recognized, among other things, the need for a treatment planning system that can determine a high-quality treatment plan in real time (e.g. providing a treatment plan or updated treatment plan during a patient workflow), such as to improve patient workflows (e.g., reduce a patient wait time to receive a radiation treatment) and to provide for rapid radiation treatment therapy replanning (e.g., a treatment plan can be recalculated or updated based changes in a patient). A high quality treatment plan can be a treatment plan that satisfies the treatment plan prescription, e.g., a plan that irradiates the target to the extent intended by the prescribing physician, and that spares the OARs as much as possible or to the extent specified in the treatment plan constraints. A treatment plan can include an intensity modulated radiotherapy treatment plan or a volumetric modulated arc therapy treatment plan. These constraints are usually depicted as dose volume histograms (DVHs) displaying the cumulative dose per volume fraction of target or OAR volume, and fractional dose to fractional target/OAR volume as described above. The present inventors have also recognized that it is possible to train a neural network, such as a deep convolutional neural network to determine machine parameters for a radiation therapy treatment plan based on imaging information. The neural network can learn the properties of treatment plans for a common diagnosis and can predict the likely treatment machine parameter settings, such as to deliver the intended dose distributions. The machine parameters can include gantry angles, beam apertures (e.g., beam section shapes) through which the therapeutic X-ray beams can be projected at a target, and the aperture intensities. The neural network can estimate the machine parameters to drive the treatment machine, based on the image of the patient and the target and OAR delineations. The neural network can include a model with linkages between patient anatomies and treatment constraints, and the treatment machine parameter settings that can deliver the intended 3D dose distribution. The trained neural network can provide a model of the treatment planning process that can encapsulate the many subjective decisions made during plan creation, and can enable the production of plan templates to initiate plan creation, provide an assessment of plan quality, provide aid for treatment clinics lacking deep local IMRT/VMAT expertise, and perhaps in the future provide fully automated treatment planning.

In an aspect, the disclosure can feature a method for training a deep convolutional neural network, such as to provide a patient radiation treatment plan. The method can include collecting patient data from a group of patients. The patient data can include at least one image of patient anatomy and a prior treatment plan. The treatment plan can include predetermined machine parameters. The method can also include training a deep convolution neural network for regression by using the prior treatment plans and the corresponding collected patient data, such as to determine a new treatment plan. The new treatment plan can include predicted machine parameters. The method can also include training the deep convolutional neural network by adjusting one or more parameters of the deep convolutional neural network, such as to minimize a cost function that includes a difference between the predetermined sets of machine parameters and predicted sets of machine parameters. The predetermined machine parameters can include at least one of a gantry angle, a multi-leaf collimator leaf position, or a radiation therapy beam intensity. The predicted machine parameters can include at least one of a gantry angle, a multi-leaf collimator leaf position, or a radiation therapy beam intensity. The method can also include collecting patient data including at least one signed distance map from each patient in a group of patients. The at least one image of patient anatomy can include at least one of a planning CT image, an anatomy label map, a determined object distance such as a signed distance map from the patient.

In an aspect, the disclosure can feature a method of using a deep convolutional neural network, such as to provide a radiation treatment plan. The method can include retrieving a trained deep convolution neural network previously trained on patient data from a group of patients. The method can also include collecting new patient data. The new patient data can include at least one image of patient anatomy. The method can also include determining a new treatment plan for the new patient using the trained deep convolutional neural network for regression. The new treatment plan can include a new set of machine parameters. The trained deep convolutional neural network can provide the new treatment plan including the set of machine parameters. The set of machine parameters can include at least one of a gantry angle, a multi-leaf collimator leaf position, or a radiation therapy beam intensity. The new treatment plan can be created in real-time. The new treatment plan can be created in real-time during a radiation therapy treatment. A treatment plan that can be created in real-time during a radiation therapy treatment can include an online adaptive plan.

In an aspect, the disclosure can feature a radiation therapy treatment system. The system can include an image acquisition device, such as to collect patient data including at least one image of patient anatomy. The system can also include a radiation therapy device, such as to deliver radiation therapy to a patient. The system can also include a non-transitory machine-readable medium, such as to store a trained deep convolution neural network and radiation therapy treatment plans. The system can also include a processor, such as to generate a new treatment plan based on the collected patient data using the trained deep convolution neural network for regression. The new treatment plan can include a set of machine parameters. The system can also include a radiation therapy control circuit that can be configured to instruct the radiation therapy device to deliver radiation therapy to the patient in accordance with the new radiation treatment plan having a new set of machine parameters. The trained deep convolution neural network can be configured to be previously trained on patient data from a group of patients. The new set of machine parameters can include predicted machine parameters. The new set of machine parameters can include at least one of a gantry angle, a multi-leaf collimator leaf position, or a radiation therapy beam intensity. The deep convolutional neural network can be trained by adjusting one or more parameters of the deep convolutional neural network, such as to minimize a cost function that can include a difference between a predetermined set of machine parameters and a predicted set of machine parameters. Patient data can include at least one signed distance map from each patient in a group of patients. The at least one image of patient anatomy can include at least one of a planning CT image, an anatomy label map, a determined object distance such as a signed distance map from the patient. The new treatment plan can be created in real-time. The new treatment plan can be created in real-time during a radiation therapy treatment.

In an aspect, the disclosure can feature a non-transitory machine-readable medium including instructions, which when executed by an image processor, cause the image processor to receive patient data from a group of patients. The patient data can include at least one image of patient anatomy and a prior treatment plan. The treatment plan can include predetermined machine parameters. The non-transitory machine readable medium can also include instructions, which when executed by the image processor, cause the image processor to train a deep convolution neural network for regression by using the prior treatment plans and the corresponding collected patient data. The at least one or more parameters of the deep convolution neural network can be adjusted to minimize a cost function. The non-transitory machine readable medium can also include instructions, which when executed by the image processor, cause the image processor to determine a new treatment plan that can include a new set of predicted machine parameters using the trained deep convolution neural network. The machine parameters can include at least one of a gantry angle, a multi-leaf collimator leaf position, or a radiation therapy beam intensity. The non-transitory machine readable medium can also include instructions, which when executed by the image processor, cause the image processor to receive patient data that can include at least one signed distance map from each patient in a group of patients. The at least one image of patient anatomy can include at least one of a planning CT image, an anatomy label map, or a determined object distance. The new treatment plan can be created in real-time during a radiation therapy treatment.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Figure 1:
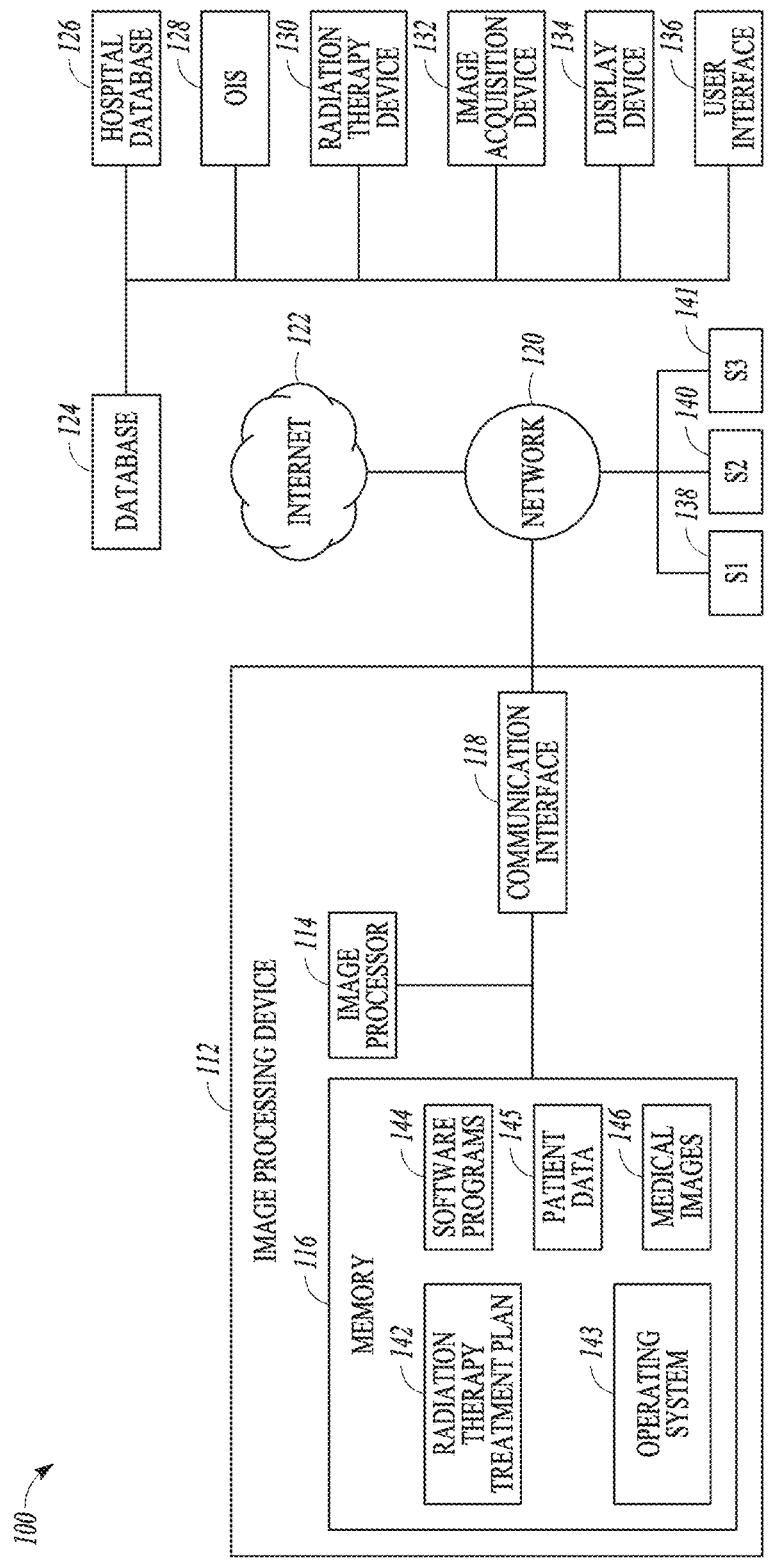
FIG. 1 illustrates an exemplary radiotherapy system, according to some embodiments of the present disclosure.

FIG. 1 illustrates an exemplary radiotherapy system 100 for providing radiation therapy to a patient. The radiotherapy system 100 includes an image processing device, 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114 and a communication interface 118. The memory device 116 may store computer-executable instructions, such as an operating system 143, a radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114. In one embodiment, the software programs 144 may convert medical images of one format (e.g., MRI) to another format (e.g., CT) by producing synthetic images, such as a pseudo-CT image. For instance, the software programs 144 may include image processing programs to train a predictive model for converting a medial image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target, or any other structural aspect useful to neural network learning. The memory device 116 may store data, including medical images 146, patient data 145, and other data required to create and implement a radiation therapy treatment plan 142.

In addition to the memory 116 storing the software programs 144, it is contemplated that software programs 144 may be stored on a removable computer medium, such as a hard drive, a computer disk, a CD-ROM, a DVD, a HD, a Blu-Ray DVD. USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software 144 when executed may train a boundary detector, or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art. In some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 114 can execute sequences of computer program instructions, stored in memory 116, to perform various operations, processes, methods that will be explained in greater detail below.

The memory device 116 can store medical images 146. In some embodiments, the medical images 146 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 146 may be received and stored in any type of data or any type of format that the image processing device 112 may use to perform operations consistent with the disclosed embodiments. The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory 116. The Communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtain CT images (e.g., medical images 146). In addition, network 120 may be connected to internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted, received via network 120, through communication interface 118 in order to be accessed by the processor 114, as required.

The image processing device 112 may communicate with database 124 through network 120 to send/receive a plurality of various types of data stored on database 124. For example, database 124 may include machine data that is information associated with a radiation therapy device 130, image acquisition device 132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 124 received from image acquisition device 132. Database 124 may store data to be used by the image processor 114 when executing software program 144, or when creating radiation therapy treatment plans 142. Database 124 may store the data produced by the trained neural network including the network parameters constituting the model learned by the network and the resulting predicted data. The image processing device 112 may receive the imaging data 146 (e.g., 2D MRI slice images, CT images, 2D Fluoroscopy images, X-ray images, 3DMRI images, 4D MRI images, etc.) either from the database 124, the radiation therapy device 130 (e.g., a MRI-Linac), and or the image acquisition device 132 to generate a treatment plan 142.

In an embodiment, the radiotherapy system 100 can include an image acquisition device 132 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 132 can be stored within database 124 as either imaging data and/or test data. By way of example, the images acquired by the imaging acquisition device 132 can be also stored by the image processing device 112, as medical image data 146 in memory 116.

In an embodiment, for example, the image acquisition device 132 may be integrated with the radiation therapy device 130 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130. "Real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as beam angles, dose-histogram-volume information, the number of radiation beams to be used during therapy, the dose per beam, and the like.

The image processor 114 may generate the radiation therapy treatment plan 142 by using software programs 144 such as treatment planning software, such as Monaco®, manufactured by Elekta AB of Stockholm, Sweden. In order to generate the radiation therapy treatment plans 142, the image processor 114 may communicate with the image acquisition device 132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images. SPECT images and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR, defining 95% of dose to the target tumor, defining that the spinal cord, brain stem, and optic structures receive ≤45Gy, ≤55Gy and <54Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer, e.g., Apple iPad®, Lenovo Thinkpad®, Samsung Galaxy®, etc.

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

Figure 2A:
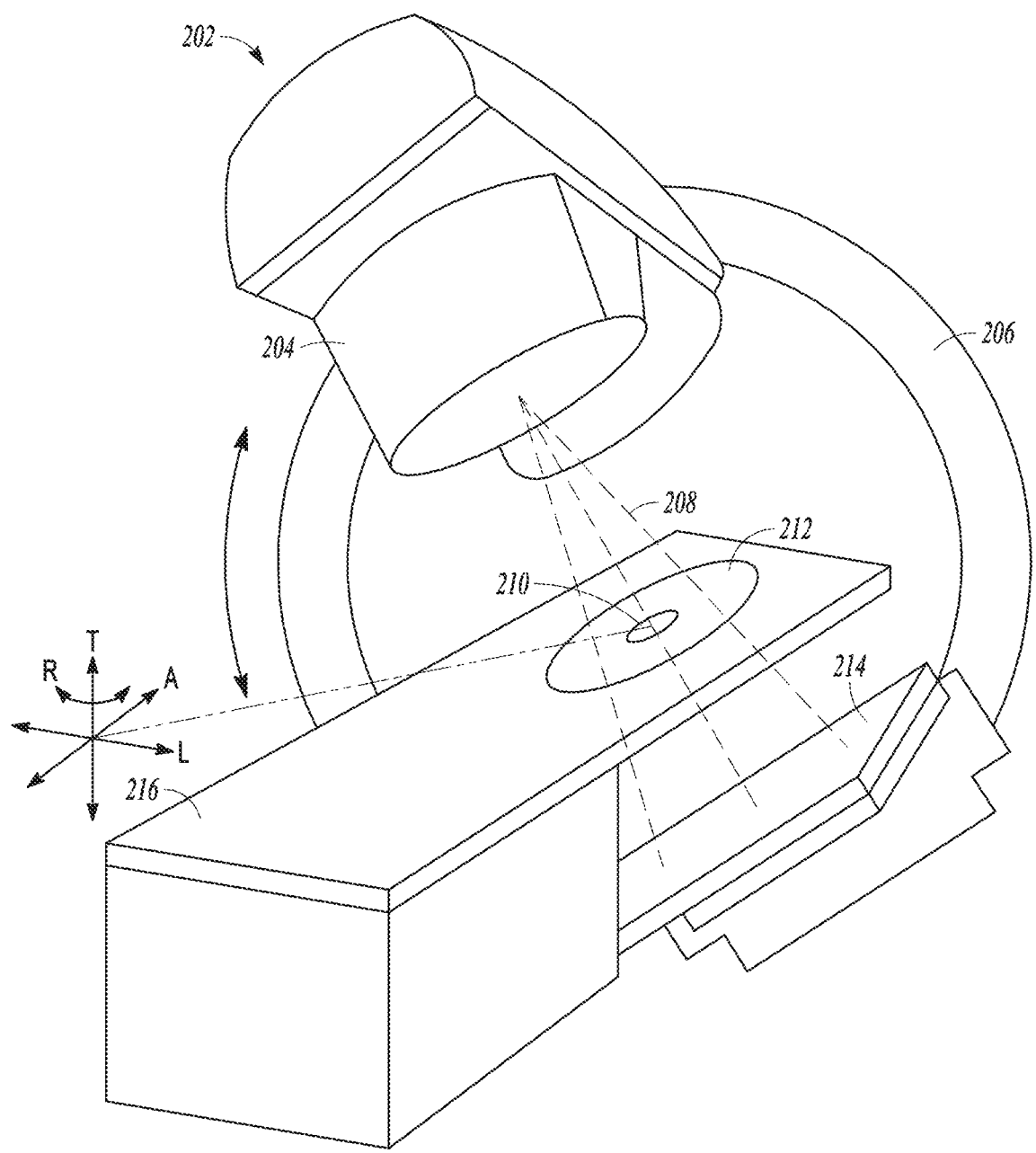
FIG. 2A illustrates an exemplary radiation therapy system that can include radiation therapy output configured to provide a therapy beam.

FIG. 2A illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC) as described in the illustrative embodiment of FIG. 5, below.

Referring back to FIG. 2A, a patient can be positioned in a region 212, supported by the treatment couch 216 to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2A can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Figure 2B:
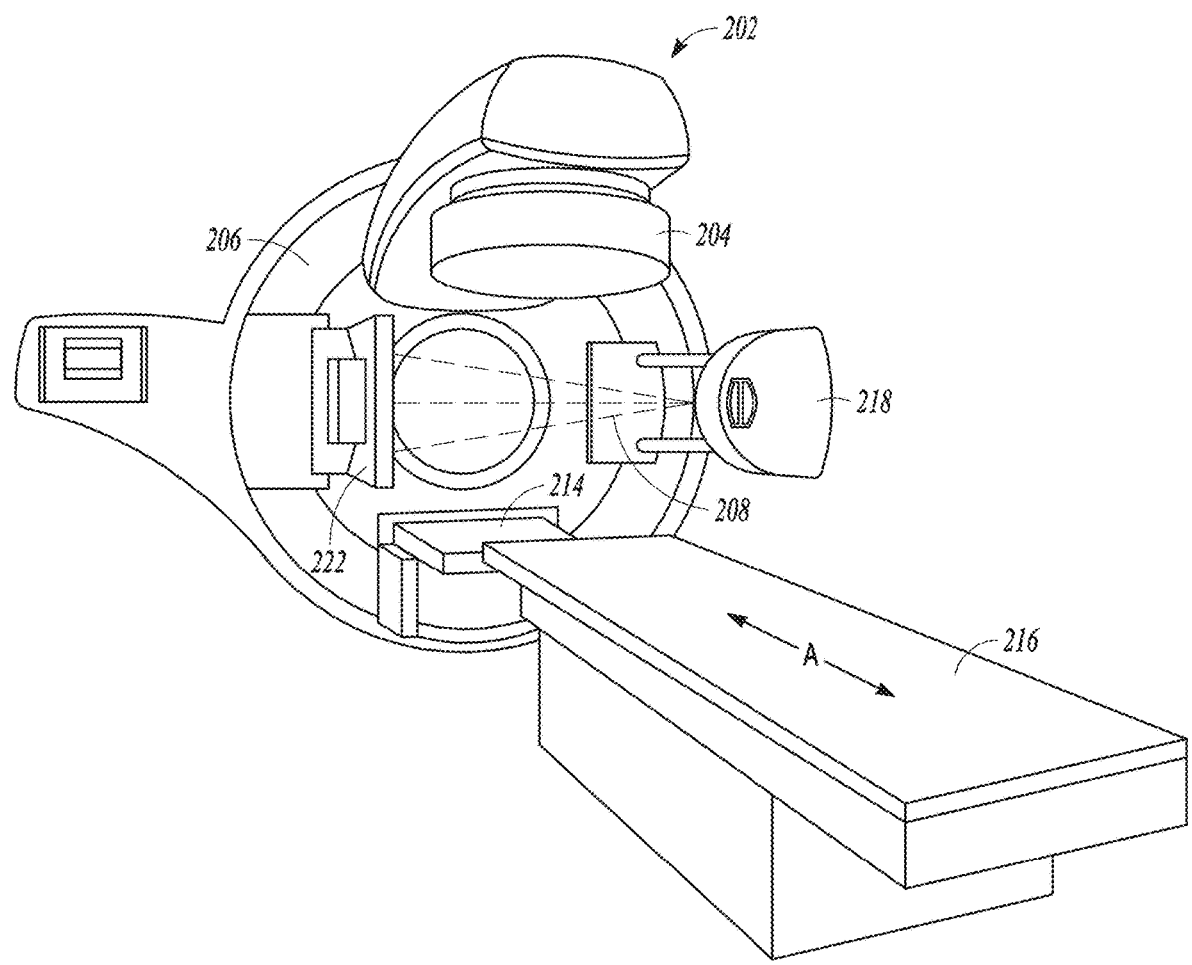
FIG. 2B illustrates an exemplary system including a combined radiation therapy system and an imaging system, such as a cone beam computed tomography (CBCT) imaging system.

FIG. 2B illustrates an exemplary radiation therapy device 202 that may include a combined linear accelerator and an imaging system, such as can include a computed tomography (CT) imaging system. The radiation therapy device 202 can include a multi-leaf collimator (not shown). The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy system 202 can be similar to the system 202 described in relation to FIG. 2A, such as including a radiation therapy output 204, a gantry 206, a platform 216, and another flat panel detector 214. The X-ray source 218 can provide a comparatively-lower-energy X-ray diagnostic beam, for imaging.

In the illustrative embodiment of FIG. 2B, the radiation therapy output 204 and the X-ray source 218 can be mounted on the same rotating gantry 206, rotationally-separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
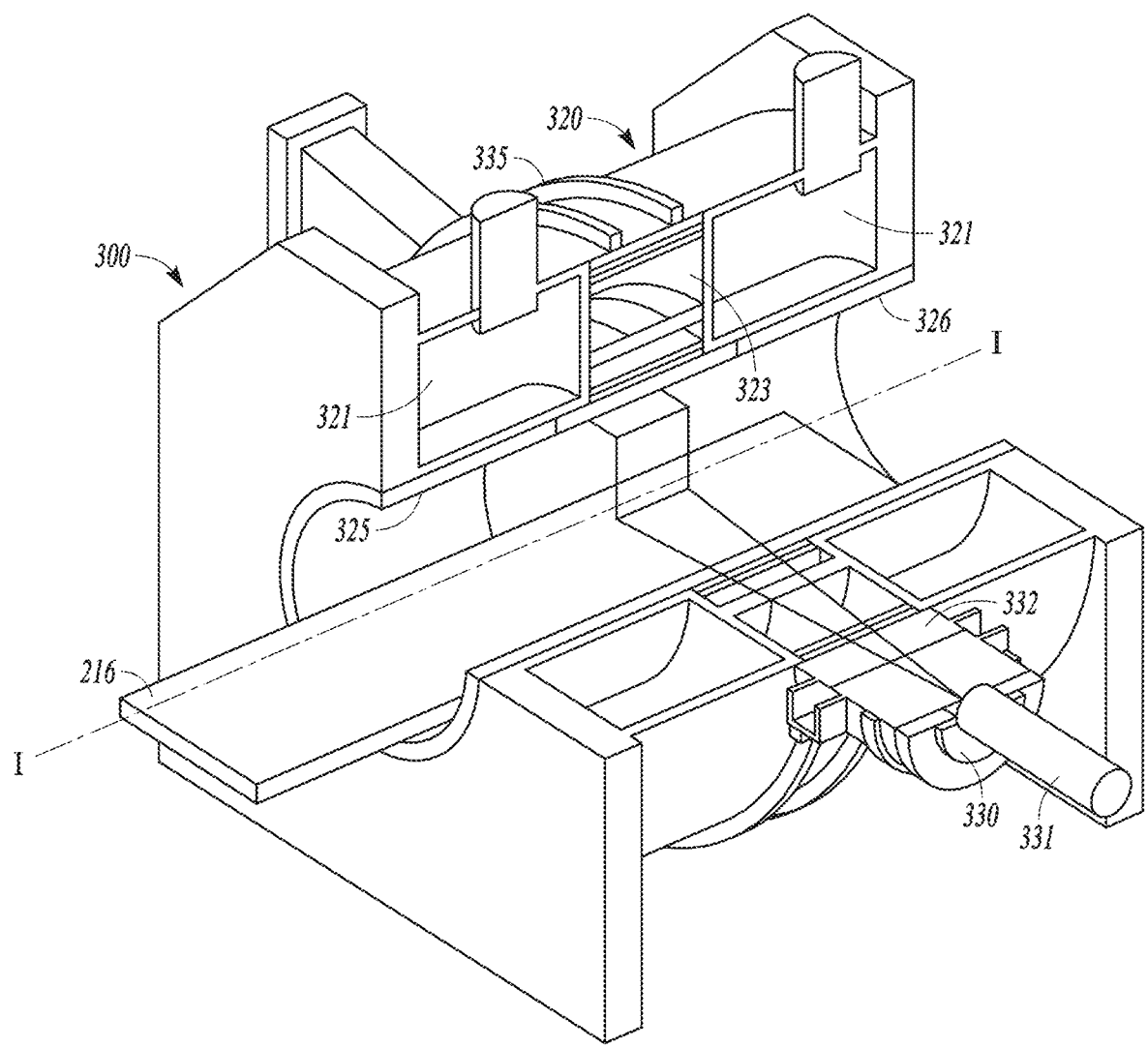
FIG. 3 illustrates a partially cut-away view of an exemplary system including a combined radiation therapy system and an imaging system, such as a nuclear magnetic resonance (MR) imaging system.
Figure 4A:
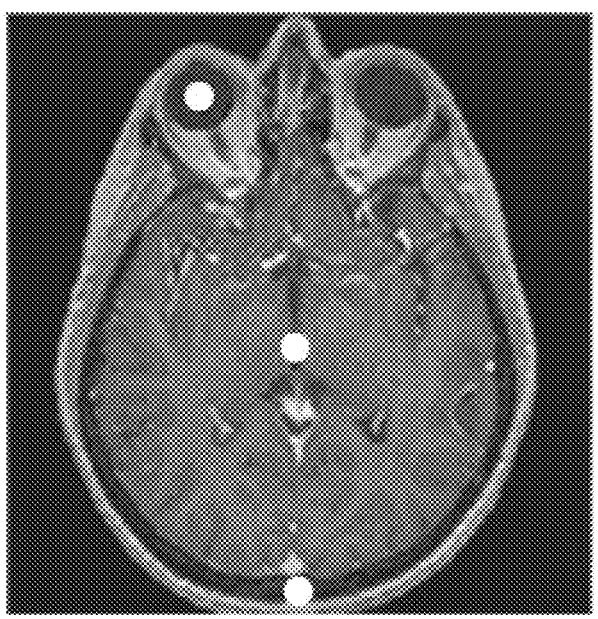
FIGS. 4A and 4B depict the differences between an exemplary MRI image and a corresponding CT image, respectively.
Figure 4B:
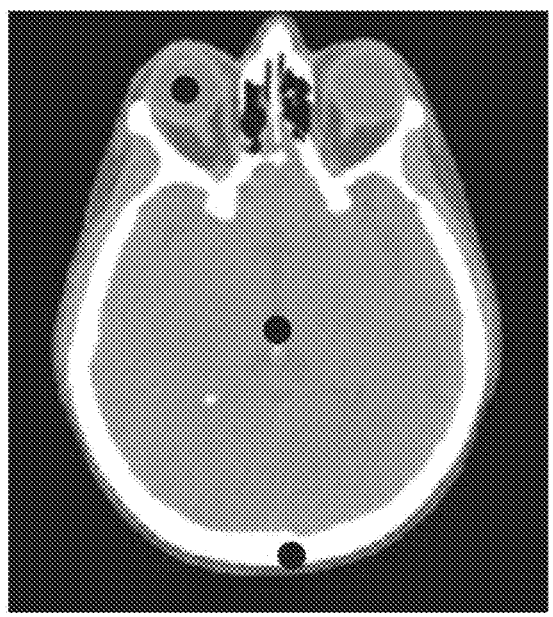

FIG. 3 depicts an exemplary radiation therapy system 300 that can include combining a radiation therapy device 202 and an imaging system, such as a nuclear magnetic resonance (MR) imaging system (e.g., known in the art as a MR-Linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal, translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321, and may be displaced along that central axis. The displacement may create a gap, or window, between coils 325 and 326. In embodiments where magnet 321 can also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 320 concerns certain embodiments and is not intended to be limiting.

Figure 5:
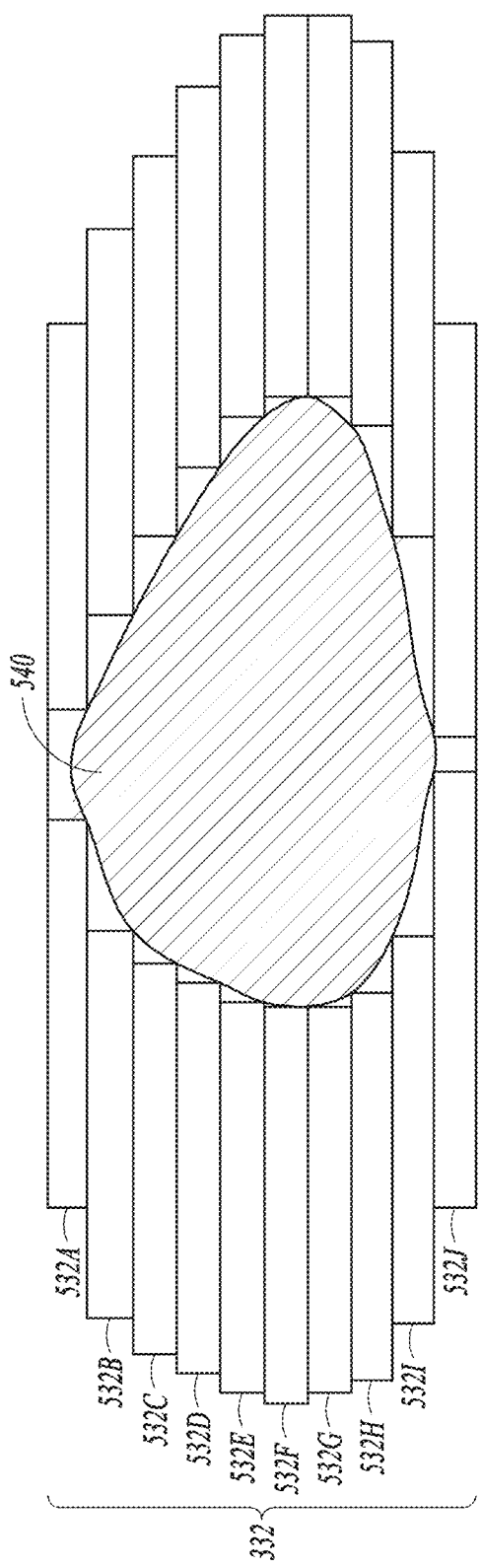
FIG. 5 illustrates an exemplary collimator configuration for shaping, directing, or modulating an intensity of a radiation therapy beam.

Radiotherapy device 330 may include the source of radiation 331, such as an X-ray source or a linear accelerator, and a multi-leaf collimator (MLC) 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216, when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnetic coils 321, 325, 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally illustrate embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include a multi-leaf collimator for shaping, directing, or modulating an intensity of a radiation therapy beam to the specified target locus within the patient. FIG. 5 illustrates an exemplary multi-leaf collimator (MLC) 332 that includes leaves 532A through 532J that can be automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction, and having ends oriented orthogonally to the beam direction (as shown in the plane of the illustration of FIG. 2A). A "state" of the MLC 332 can be adjusted adaptively during a course of radiation therapy treatment, such as to establish a therapy beam that better approximates a shape or location of the tumor 540 or other target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as Intensity Modulated Radiation Therapy (IMRT).

Figure 6:
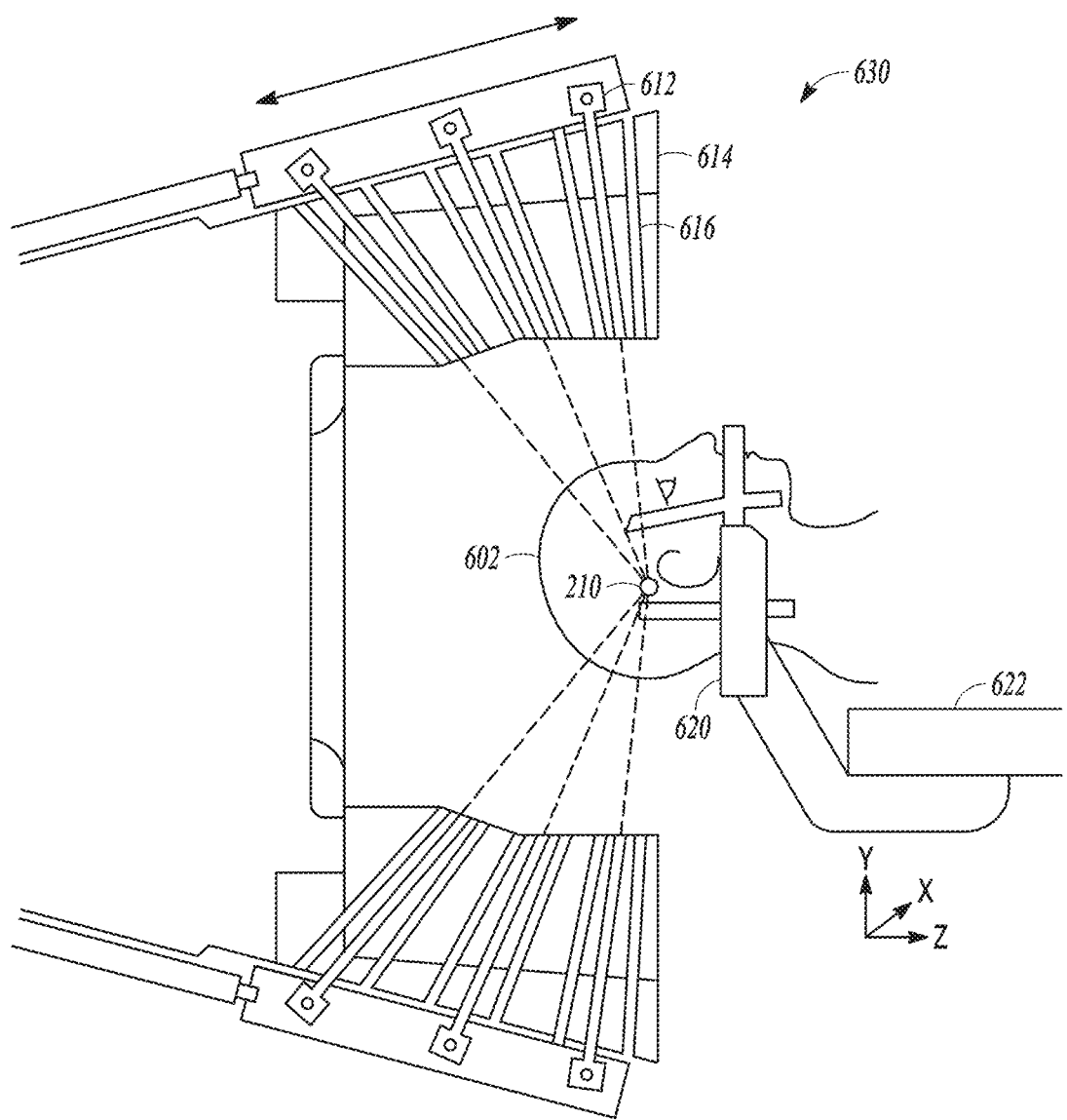
FIG. 6 illustrates an exemplary Gamma knife radiation therapy system.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7:
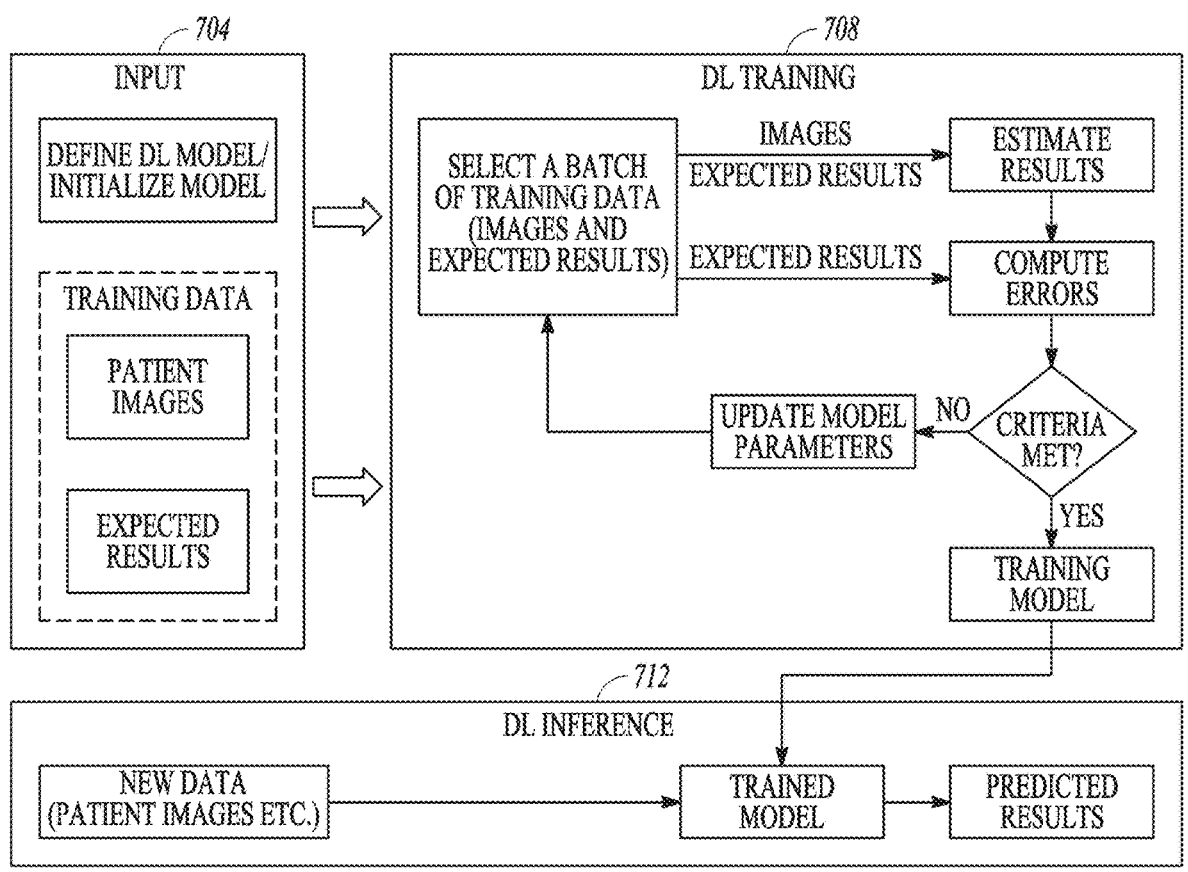
FIG. 7 illustrates an exemplary flow diagram for deep learning.

FIG. 7 illustrates an exemplary flow diagram for deep learning, where a deep learning model, such as a deep convolutional neural network can be trained and used to determine machine parameters for a treatment plan. Inputs 704 can include a defined deep learning model having an initial set of values and training data. The training data can include patient images, and expected results. The training data can also include data based on the patient images, such as one or more of anatomy label maps or signed distance maps. The deep learning model can include a neural network, such as a deep convolutional neural network. The deep learning network can be trained on medical images, such as CT images, PET images, or MRI images and the corresponding treatment machine parameters produced by an exemplary planning method. When trained, the deep learning network can produce an estimate of such machine parameters for a patient using only that patient's image. In either case, the expected results can include estimated machine parameters that can define the delivery of radiation treatment to a patient. The machine parameters can include at least one gantry angle, at least one multi-leaf collimator leaf position, and at least one aperture weight or intensity. In one embodiment, the images or functions of the images may be paired with machine parameters encoded as pixel values in a second set of images. In another embodiment, the images or image functions may be transformed into a sinogram format and paired with machine parameters that can be represented as elements of a 1D vector having a dimension that can be equal to the sinogram row dimension. During training of deep learning model 708, a batch of training data can be selected from the patient images and expected results. The selected training data can include at least one image of patient anatomy or data based on the at least one image of patient anatomy and the corresponding ground truth machine parameter data. The deep learning model can be applied to the selected patient images to provide estimated results (e.g., estimated machine parameters), which can then be compared to the expected results (e.g., machine parameters corresponding to the selected patient images), to compute a difference that can provide an indication of training errors. The errors can be used during a procedure called backpropagation to correct the errors in parameters of the deep learning network (e.g., layer node weights and biases), such as to reduce or minimize errors in the machine parameter estimates during subsequent trials. The errors can be compared to predetermined criteria, such as proceeding to a sustained minimum for a specified number of training iterations. If the errors do not satisfy the predetermined criteria, then model parameters of the deep learning model can be updated using backpropagation, and another batch of training data can be selected from the patient images and expected results for another iteration of deep learning model training. If the errors satisfy the predetermined criteria, then the training can be ended and the trained model can then be used during a deep learning testing or inference stage 712 to predict machine parameters based on patient images different from the training data. The trained model can receive new patient images and provide predicted results (e.g., machine parameters).

Figure 8:
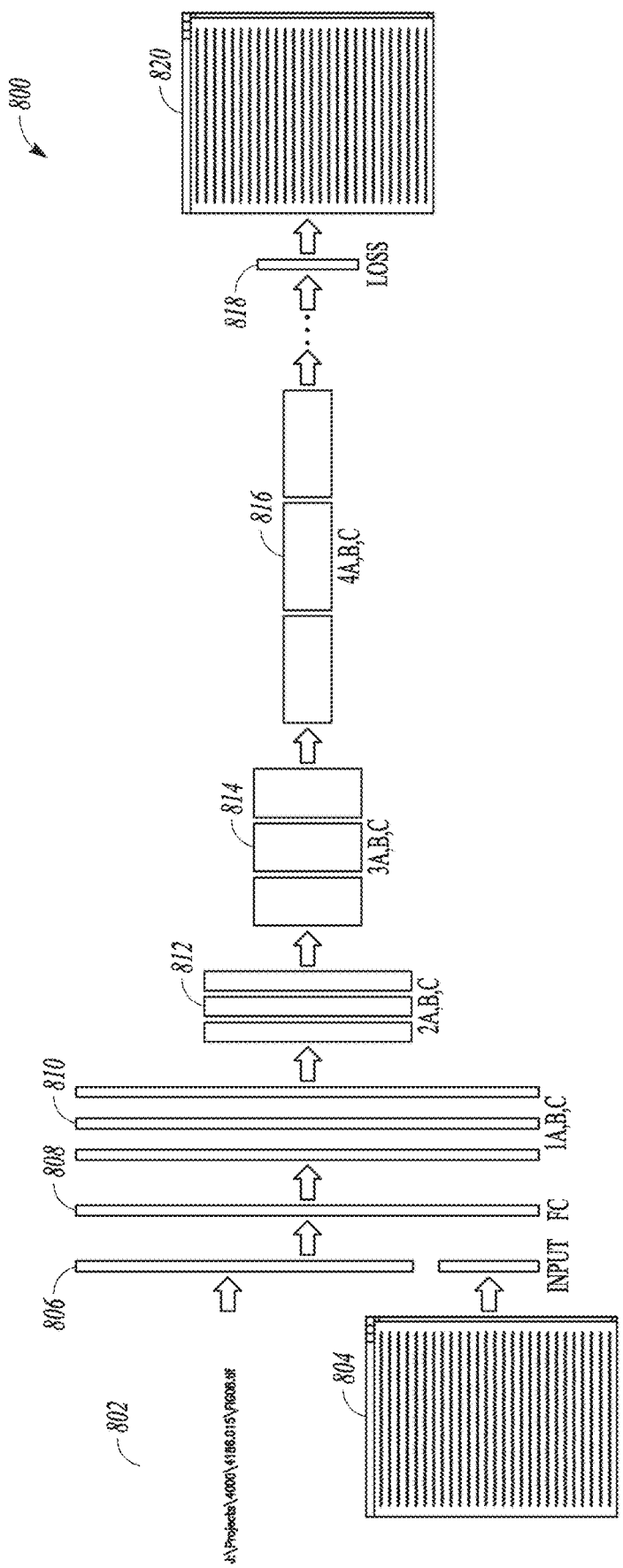
FIG. 8 illustrates an embodiment of a deep convolutional neural network.

FIG. 8 illustrates an embodiment of a deep convolutional neural network (DCNN) 800 that can be trained using sets of known images or image functions and lists of known machine parameters. Once trained, the DCNN can compute estimates of machine parameters for a new patient (e.g., a patient that did not contribute known images or image functions used in the training process) given only the new patient's images or image functions. In an embodiment, the DCNN 800 can include a DCNN for regression. The DCNN 800 can be stored in a memory, such as the memory device 116 of image processing device 112. The DCNN 800 can be comprised of layers 806, 808, sets of layers 810, 812, 814, 816, and a loss layer 818. Input image data 802 and corresponding machine parameter data 804 can be introduced into the DCNN by layers 806, that may perform scaling and centering of the data. The outputs of layers 806 can then be input into fully-connected (FC) layer 808 that can perform a mixing of the image data and the machine parameter data. The fully-connected layer 808 output can be fed into the first convolution layer in layer set 810. Each convolution layer block 810, 812, 814, and 816, can be composed of at least one convolution layer, and a nonlinearity layer (e.g., a rectified linear unit or ReLU layer) that can apply a non-linear function to the output of the convolution layer. Each block may also contain a batch normalization layer, a scaling layer or other layers that may be determined, such as to provide the most accurate estimates of desired machine parameter values. The last layer in the last block of each set can be a pooling layer that can downsample the convolution output data by an amount (e.g. one-half) and can take the maximum of the relevant layer-node values in the output convolution layer, during a process known as max-pooling. The changing shapes of each convolution block set can indicate that a spatial resolution of the image data can be decreasing (block height) while a number of parameters per layer can be increasing (block width). The arrangement of layers and the layer-set compositions illustrated in FIG. 8 can preserve the information content of the DCNN. During network training the machine parameter estimates output at the loss layer 818 can be compared to the correct machine parameter values (e.g., ground truth machine parameter values), and the differences (e.g., errors) are used to correct the network parameters. The correction process is known as backpropagation. The network parameters can be the weight coefficients and bias terms associated with the layer nodes whose values can be reset during backpropagation. During network testing, a new patient image can be input with no corresponding machine parameters, and the node weight coefficients and the biases evaluated during training can combine to produce the machine parameter estimates output at loss layer 818. The machine parameter estimates output can constitute the machine parameter estimate for a new patient.

The network depicted in FIG. 8 is illustrative only and not limiting to the method of this invention. Many other network architectures are possible, and one or more of them may provide improved machine parameter estimates. In another embodiment, the input image data can include CT images, or functions of the CT images such as signed distance functions, or modified images obtained by filtering, re-formatted into a sinogram format representing the patient geometry as circular projections to be paired with a vector of angular-resampled machine parameter data and input as a pair of 1D vectors at the input layer. In another embodiment, the fully connected layer (FC) can be moved closer to the loss layer, and a pair of convolutional networks, one each for the image and machine parameter data, can be established and trained in parallel. In another embodiment, the FC layer can be removed and spatial associations of the patient geometry and the machine parameter gantry angle and multileaf collimator settings can be established by 2D convolution layers that explicitly embed functions of the 1D data. In another embodiment, a second convolutional neural network can be used to learn a refined-value version of the machine parameters using the patient images or image functions and the machine parameter errors from the first network. In another embodiment, a convolutional neural network can learn the machine parameters using a combination of patient images or image functions and images of the 3D dose distribution corresponding to the ground truth machine parameters—such additional channels of information may produce machine parameter estimates having improved accuracy.

Figures 9A, 9B:
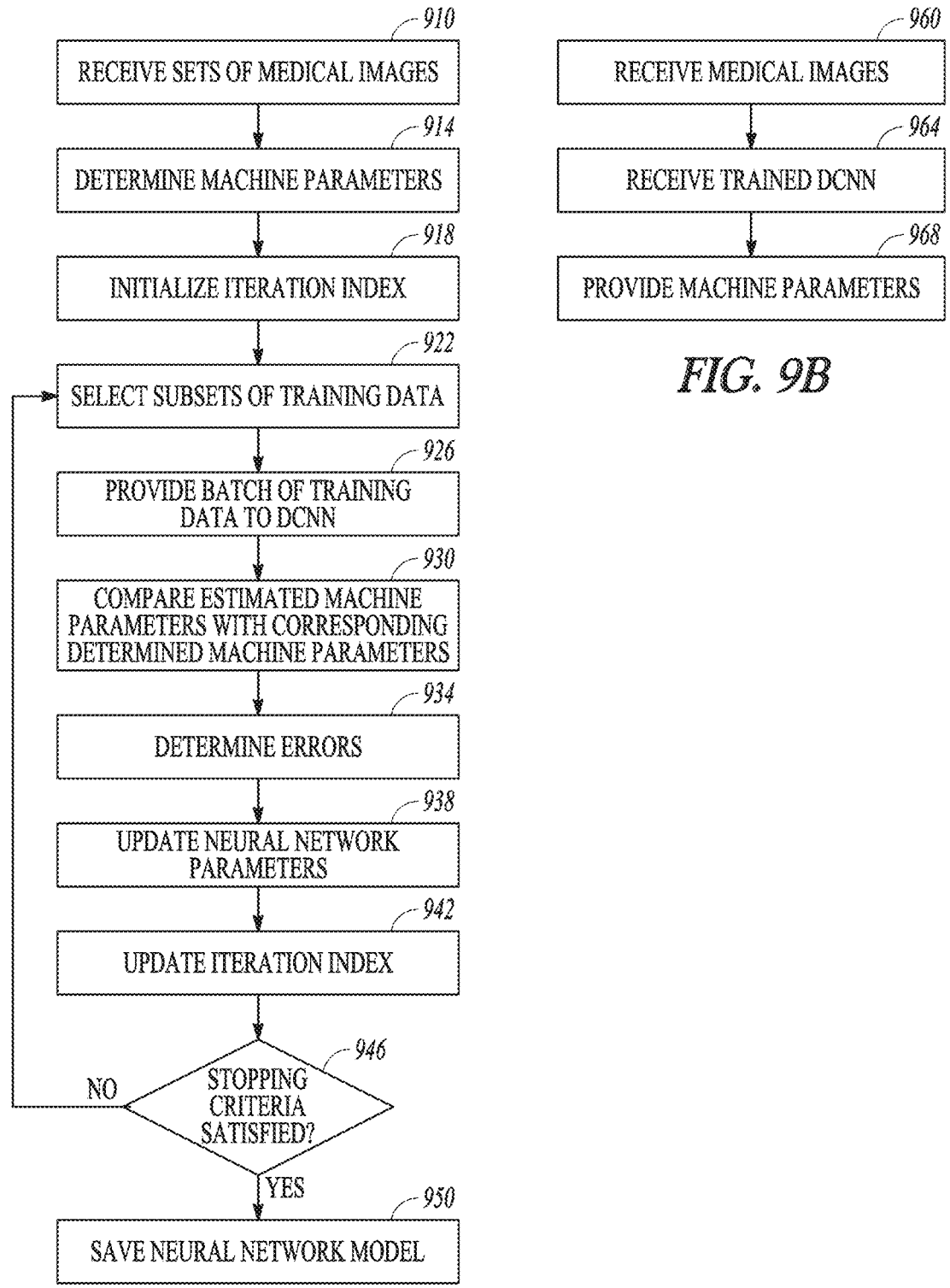
FIG. 9A illustrates an exemplary method for training a DCNN.
FIG. 9B illustrates an exemplary method for generating artifact reduced, reconstructed 3D images using a trained DCNN.

FIG. 9A illustrates an embodiment of a method for training a DCNN, such as the DCNN 800 for determining a set of machine parameters based on at least one medical image. The DCNN can receive sets of medical images (step 910). The medical images can include CT images, MRI images, or PET images. The DCNN can also receive corresponding anatomy voxel label maps, and functions of labelled object distances. Machine parameters can then be determined for each set of medical images (step 914). In an embodiment, the machine parameters can be received together with the sets of medical images. The machine parameters can include at least one gantry angle, at least one multi-leaf collimator leaf position, and at least one aperture weight or intensity. The machine parameters can be represented by the expression $Y=\{\varphi,(\ldots L_n^\varphi R_n^\varphi \ldots )^T, y^\varphi\}_k$, $k=1, \ldots, K$, where Y can represent a set of K machine parameter data objects, $\varphi$ can represent a gantry angle. $L_n^\varphi R_n^\varphi$ can represent left and right multi-leaf collimator leaf positions, and $y^\varphi$ can represent an aperture weight or intensity for a gantry angle $\varphi$. The machine parameters can be determined by a computer algorithm or a dosimetrist operating a radiotherapy treatment program, either of which can be very time consuming and complicated and may not be suitable for real time applications. In an embodiment where the machine parameters can be determined by a computer algorithm, the algorithm can be an iterative or analytical algorithm and the computation can require several hours per patient. And for neither case does there exist a model against which the operator may judge his/her treatment plan quality. To begin network training, an iteration index can be set to an initial value of zero (step 918). A batch of training data can be formed from a subset of the received sets of medical images and corresponding machine parameters (step 922). The batch of training data can be provided to the DCNN and the DCNN parameters can be updated based thereon (step 926). The DCNN can provide an output set of machine parameters based on current parameters of the DCNN (step 930). A comparison can be made between the output set of machine parameters corresponding to the received sets of medical images in the batch of training data (e.g., ground truth machine parameters). Corresponding error sets, where each error value can be the difference between the estimated machine parameters and the corresponding ground truth machine parameters are determined from the comparison (step 934). Parameters of the DCNN can then be updated based on the corresponding errors, such as by using back-propagation (step 938). In an embodiment, parameters of the DCNN can be updated, such as to minimize or reduce a cost function, such as the cost function $J(\Theta^*)=\arg\min_\Theta \|Y-Y^*\|^2$, where Y can represent the machine parameters determined by the DCNN, where Y* can represent the known machine parameters corresponding to the batch of training data, and where $\Theta^*$ can represent parameters of the DCNN (e.g., layer node weights and biases as described above above) corresponding to a minimized square error between Y and Y*. In an embodiment, the cost function can include a probabilistic function where parameters of the DCNN can be determined according to the expression $\Theta_{OPT}=\arg\max_\Theta P(Y|X;\Theta)$, or $\Theta_{OPT}=\arg\max_\Theta \Sigma_{t\in T} \log P(Y_t|X_t;\Theta)$ where $\Theta_{OPT}$ can represent the parameters of the fully trained DCNN, and X can represent a collection of medical images, anatomy voxel label maps, and functions of the labelled object distances.

After updating the parameters of the DCNN, the iteration index can be incremented by a value of one (step 942). The iteration index can correspond to a number of times that the parameters of the DCNN have been updated. Stopping criteria can be computed (step 946), and if the stopping criteria are satisfied, then the DCNN model can be saved in a memory, such as the memory device 116 of image processing device 112 and the training can be halted (step 950). If the stopping criteria are not satisfied, then the training can continue at step 922. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output set of machine parameters (e.g. the stopping criteria can include whether the difference between the output set of machine parameters and the machine parameters corresponding to the received sets of medical images in the batch of training data is smaller than a threshold). In an embodiment, the threshold can correspond to an asymptotic minimum of all errors determined in step 934. In an embodiment, the machine parameters can be presented to the DCNN in the form of images with fixed formats specifying, for example, apertures, angles, and intensity values. In an embodiment, the patient images can be pooled with machine parameters and can be presented as real arrays.

FIG. 9B illustrates a method for generating machine parameters using a trained DCNN, such as a DCNN that can be trained according to the method described above with respect to FIG. 9A. Medical images can be received from an image acquisition device, such as image acquisition device 132 (step 960). A trained DCNN model can be received from a network, such as the network 120, or from a memory, such as the memory device 116 of image processing device 112 (step 964). The trained DCNN can be used to determine machine parameters, such as for radiation treatment planning or replanning (step 968). In an embodiment, the trained DCNN can generate machine parameters for online applications, in real time (e.g. the trained DCNN can generate machine parameters from the received medical images in a few seconds). In an embodiment where the DCNN can be trained using machine parameters determined for intensity modulated radiotherapy, the trained DCNN can determine machine parameters for an intensity modulated radiotherapy treatment plan. In an embodiment where the DCNN can be trained using machine parameters determined for a volumetric modulated arc therapy, the trained DCNN can determine machine parameters for a volumetric modulated arc therapy treatment plan.

Figure 10:
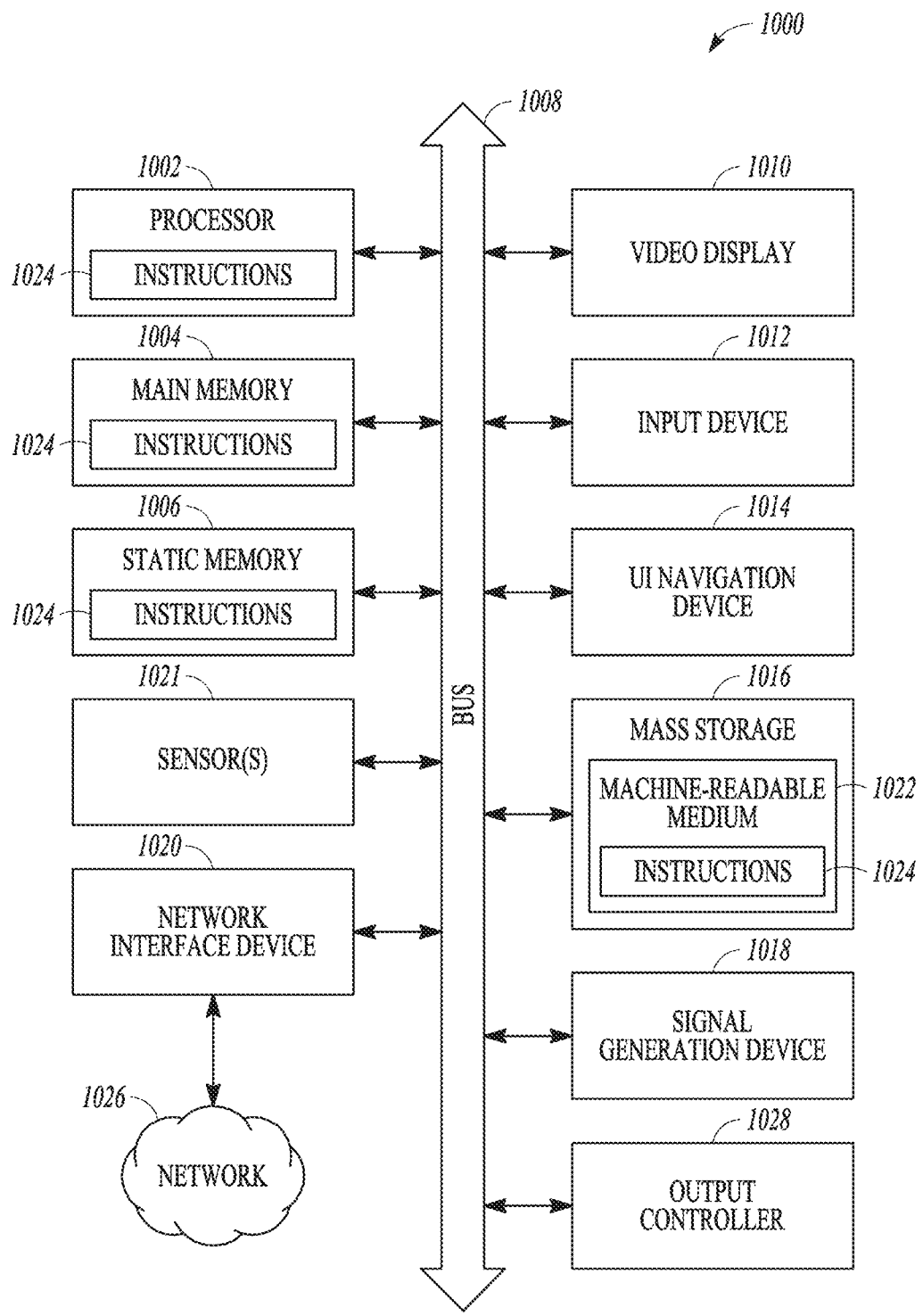
FIG. 10 illustrates an exemplary block diagram of a machine on which one or more of the methods as discussed herein can be implemented.

FIG. 10 illustrates a block diagram of an embodiment of a machine 1000 on which one or more of the methods as discussed herein can be implemented. In one or more embodiments, one or more items of the image processing device 112 can be implemented by the machine 100. In alternative embodiments, the machine 1000 operates as a standalone device or may be connected (e.g., networked) to other machines. In one or more embodiments, the image processing device 112 can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 includes processing circuitry 1002 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. The machine 1000 (e.g., computer system) may further include a video display unit 1010 (e.g., a liquid crystal display (LCD) or a cathode ray tube (CRT)). The machine 1000 also includes an alphanumeric input device 1012 (e.g., a keyboard), a user interface (UI) navigation device 1014 (e.g., a mouse), a disk drive or mass storage unit 1016, a signal generation device 1018 (e.g., a speaker) and a network interface device 1020.

The disk drive unit 1016 includes a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated includes an output controller 1028. The output controller 1028 manages data flow to/from the machine 1000. The output controller 1028 is sometimes called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document, for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

Embodiments of the invention may be implemented with computer-executable instructions. The computer-executable instructions (e.g., software code) may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media. CDROMS, magnetic-optical disks, removable optical disks (e.g., compact disks and digital video disks), flash memory devices, magnetic cassettes, memory cards or sticks (e.g., secure digital cards), random access memories (RAMs) (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the invention, the method of creating a component or module can be implemented in software, hardware, or a combination thereof. The methods provided by various embodiments of the present invention, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A method for training a deep convolutional neural network to provide a patient radiation treatment plan, the method comprising:
    collecting patient data from a group of patients, the patient data including at least one image of patient anatomy and a prior treatment plan, wherein the treatment plan includes predetermined machine parameters;
    associating a collection of the patient data with a respective set of ground-truth radiotherapy treatment machine parameters; and
    training a deep convolution neural network (DCNN) for regression by receiving the collected patient data and the associated respective set of ground-truth radiotherapy treatment machine parameters to determine a new treatment plan, the DCNN being trained to store one or more parameters that establish a relationship between the collection of training medical images, corresponding to the group of patients, and the respective set of ground-truth radiotherapy treatment machine parameters, the DCNN being trained to process a given one of the collection of training medical images to predict an output comprising two or more estimated radiotherapy treatment machine parameters, and the training comprising comparing the two or more estimated radiotherapy treatment machine parameters, that were predicted by the DCNN processing the given one of the collection of training medical images, with a given group of two or more of the set of ground-truth radiotherapy treatment machine parameters corresponding to the given one of the collection of training medical images.

2. The method of claim 1, wherein the new treatment plan comprises predicted machine parameters, wherein training the DCNN comprises:
    receiving training data comprising the collection of training medical images and the respective set of ground-truth radiotherapy treatment machine parameters, the set of ground-truth radiotherapy treatment machine parameters being generated using a treatment planning process prior to training the DCNN and being received together with the training medical images;
    for each batch of training data comprising at least one training medical image of the collection of training medical images and a given set of ground-truth radiotherapy treatment machine parameters:
    applying the DCNN to the at least one training medical image to generate a set of estimated radiotherapy treatment machine parameters;
    comparing the set of estimated radiotherapy treatment machine parameters with the given set of ground-truth radiotherapy treatment machine parameters; and
    updating the one or more parameters of the DCNN based on a result of comparing the set of estimated radiotherapy treatment machine parameters with the given set of ground-truth radiotherapy treatment machine parameters; and
    applying the DCNN with the updated one or more parameters to another batch of the training data.

3. The method of claim 1, further comprising:
    prior to training the DCNN:
    obtaining a first training medical image from the collection of training medical images;
    applying a radiotherapy treatment planning process to generate a first set of ground-truth radiotherapy treatment machine parameters based on the first training medical image; and
    forming a training data pair comprising the first training medical image and the generated first set of ground-truth radiotherapy treatment machine parameters;
    receiving, by the DCNN, the first training medical image and the generated first set of ground-truth radiotherapy treatment machine parameters together as the formed training data pair; and
    training the deep convolutional neural network, based on training data pair comprising the first training medical image and the generated first set of ground-truth radiotherapy treatment machine parameters, by adjusting the one or more parameters of the deep convolutional neural network to minimize a cost function that includes a difference between the predetermined sets of machine parameters comprising the first set of ground-truth radiotherapy treatment machine parameters and predicted sets of machine parameters generated based on the first training medical image.

4. The method of claim 2, wherein the predetermined machine parameters include at least one of a gantry angle, a multi-leaf collimator leaf position, or a radiation therapy beam intensity, wherein the treatment planning process used to generate the set of ground-truth radiotherapy treatment machine parameters excludes the DCNN, a result of generating the set of ground-truth radiotherapy treatment machine parameters using the treatment planning process that excludes the DCNN being used to train the DCNN to predict the radiotherapy treatment machine parameters.

5. The method of claim 3 wherein the predicted machine parameters include at least one of a gantry angle, a multi-leaf collimator leaf position, or a radiation therapy beam intensity.

6. The method of claim 1, further comprising collecting patient data including at least one signed distance map from each patient in a group of patients.

7. The method of claim 1, wherein the at least one image of patient anatomy includes at least one of a planning CT image, an anatomy label map, a determined object distance such as a signed distance map from the patient.

8. A method of using a deep convolutional neural network to provide a radiation treatment plan, the method comprising:
retrieving a trained deep convolution neural network previously trained on patient data from a group of patients;
collecting new patient data, wherein the new patient data includes at least one image of patient anatomy; and
determining a new treatment plan for the new patient using the trained deep convolutional neural network (DCNN) for regression, wherein the new treatment plan has a new set of machine parameters, the DCNN being trained to receive a collection of training medical images and associated respective set of ground-truth radiotherapy treatment machine parameters and to store one or more parameters that establish a relationship between the collection of training medical images, corresponding to the group of patients, and the respective set of ground-truth radiotherapy treatment machine parameters, the DCNN being trained to process a given one of the collection of training medical images to predict an output comprising two or more estimated radiotherapy treatment machine parameters, and the training comprising comparing the two or more estimated radiotherapy treatment machine parameters, that were predicted by the DCNN processing the given one of the collection of training medical images, with a given group of two or more of the set of ground-truth radiotherapy treatment machine parameters corresponding to the given one of the collection of training medical images.

9. The method of claim 8, wherein the trained deep convolutional neural network can provide the new treatment plan including the set of machine parameters, wherein the set of machine parameters includes at least one of a gantry angle, a multi-leaf collimator leaf position, or a radiation therapy beam intensity.

10. The method of claim 9, wherein the new treatment plan is created in real-time.

11. The method of claim 9, wherein the new treatment plan is created in real-time during a radiation therapy treatment, the DCNN being trained by:
receiving training data comprising the collection of training medical images and the respective set of ground-truth radiotherapy treatment machine parameters, the set of ground-truth radiotherapy treatment machine parameters being generated using a treatment planning process prior to training the DCNN and being received together with the training medical images;
for each batch of training data comprising at least one training medical image of the collection of training medical images and a given set of ground-truth radiotherapy treatment machine parameters:
applying the DCNN to the at least one training medical image to generate a set of estimated radiotherapy treatment machine parameters;
comparing the set of estimated radiotherapy treatment machine parameters with the given set of ground-truth radiotherapy treatment machine parameters; and
updating the one or more parameters of the DCNN based on a result of comparing the set of estimated radiotherapy treatment machine parameters with the given set of ground-truth radiotherapy treatment machine parameters; and
applying the DCNN with the updated one or more parameters to another batch of the training data.

12. A radiation therapy treatment system comprising:
an image acquisition device to collect patient data including at least one image of patient anatomy;
a radiation therapy device to deliver radiation therapy to a patient;
a non-transitory machine-readable medium to store a trained deep convolution neural network and radiation therapy treatment plans;
a processor to generate a new treatment plan based on the collected patient data using the trained deep convolution neural network (DCNN) for regression, wherein the new treatment plan includes a set of machine parameters, the DCNN being trained to receive a collection of training medical images and associated respective set of ground-truth radiotherapy treatment machine parameters and to store one or more parameters that establish a relationship between the collection of training medical images and the respective set of ground-truth radiotherapy treatment machine parameters, the DCNN being trained to process a given one of the collection of training medical images to predict an output comprising two or more estimated radiotherapy treatment machine parameters, and the training comprising comparing the two or more estimated radiotherapy treatment machine parameters, that were predicted by the DCNN processing the given one of the collection of training medical images, with a given group of two or more of the set of ground-truth radiotherapy treatment machine parameters corresponding to the given one of the collection of training medical images; and
a radiation therapy control circuit configured to instruct the radiation therapy device to deliver radiation therapy to the patient in accordance with the new radiation treatment plan having a new set of machine parameters.

13. The system of claim 12, wherein the trained deep convolution neural network is configured to be previously trained on patient data from a group of patients, the DCNN being trained by:
receiving training data comprising the collection of training medical images and the respective set of ground-truth radiotherapy treatment machine parameters, the set of ground-truth radiotherapy treatment machine parameters being generated using a treatment planning process prior to training the DCNN and being received together with the training medical images;
for each batch of training data comprising at least one training medical image of the collection of training medical images and a given set of ground-truth radiotherapy treatment machine parameters:
applying the DCNN to the at least one training medical image to generate a set of estimated radiotherapy treatment machine parameters;
comparing the set of estimated radiotherapy treatment machine parameters with the given set of ground-truth radiotherapy treatment machine parameters; and updating the one or more parameters of the DCNN based on a result of comparing the set of estimated radiotherapy treatment machine parameters with the given set of ground-truth radiotherapy treatment machine parameters; and applying the DCNN with the updated one or more parameters to another batch of the training data.

14. The system of claim 12, wherein the new set of machine parameters comprises predicted machine parameters.

15. The system of claim 12, wherein the new set of machine parameters include at least one of a gantry angle, a multi-leaf collimator leaf position, or a radiation therapy beam intensity.

16. The system of claim 12, wherein the deep convolutional neural network is trained by adjusting one or more parameters of the deep convolutional neural network to minimize a cost function that includes a difference between a predetermined set of machine parameters and a predicted set of machine parameters.

17. The system of claim 12, wherein patient data includes at least one signed distance map from each patient in a group of patients.

18. The system of claim 12, wherein the at least one image of patient anatomy includes at least one of a planning CT image, an anatomy label map, a determined object distance such as a signed distance map from the patient.

19. The system of claim 12, wherein the new treatment plan is created in real-time.

20. The system of claim 12, wherein the new treatment plan is created in real-time during a radiation therapy treatment.

21. A non-transitory machine-readable medium including instructions, which when executed by a processor, cause the processor to:

receive patient data from a group of patients, the patient data including at least one image of patient anatomy and a prior treatment plan, wherein the treatment plan includes predetermined machine parameters;

associate a collection of the patient data with a respective set of ground-truth radiotherapy treatment machine parameters;

train a deep convolution neural network (DCNN) for regression by receiving the received patient data and the associated respective set of ground-truth radiotherapy treatment machine parameters, wherein at least one or more parameters of the deep convolution neural network are adjusted to minimize a cost function, the DCNN being trained to store the one or more parameters that establish a relationship between the collection of training medical images, corresponding to the group of patients, and the respective set of ground-truth radiotherapy treatment machine parameters, the DCNN being trained to process a given one of the collection of training medical images to predict an output comprising two or more estimated radiotherapy treatment machine parameters, and the training comprising comparing the two or more estimated radiotherapy treatment machine parameters, that were predicted by the DCNN processing the given one of the collection of training medical images, with a given group of two or more of the set of ground-truth radiotherapy treatment machine parameters corresponding to the given one of the collection of training medical images; and determine a new treatment plan including a new set of predicted machine parameters using the trained deep convolution neural network, wherein the machine parameters include at least one of a gantry angle, a multi-leaf collimator leaf position, or a radiation therapy beam intensity.

22. The non-transitory machine-readable medium of claim 21, further comprising instructions, which when executed by the image processor, cause the image processor to receive patient data including at least one signed distance map from each patient in a group of patients.

23. The non-transitory machine-readable medium of claim 21, wherein the at least one image of patient anatomy includes at least one of a planning CT image, an anatomy label map, or a determined object distance.

24. The non-transitory machine-readable medium of claim 21, wherein the new treatment plan is created in real-time during a radiation therapy treatment.

* * * * *

UNITED STATES PATENT AND TRADEMARK OFFICE
CERTIFICATE OF CORRECTION

| | |
|---|---|
| PATENT NO. | : 11,517,768 B2 |
| APPLICATION NO. | : 15/658484 |
| DATED | : December 6, 2022 |
| INVENTOR(S) | : Lyndon S. Hibbard |

It is certified that error appears in the above-identified patent and that said Letters Patent is hereby corrected as shown below:

On the Title Page

On page 3, in Column 2, item [56] under "Other Publications", Line 54, delete "mages" and insert --images-- therefor Signed and Sealed this
Third Day of October, 2023

*Katherine Kelly Vidal*

Katherine Kelly Vidal
*Director of the United States Patent and Trademark Office*